(12) United States Patent
Kim et al.

(10) Patent No.: US 11,414,667 B2
(45) Date of Patent: Aug. 16, 2022

(54) HIGH EFFICIENCY APTAMER COMPLEX COMPRISING BRANCHED DNA AND APTAMER, AND USE THEREOF

(71) Applicant: POSTECH ACADEMY-INDUSTRY FOUNDATION, Pohang-si (KR)

(72) Inventors: Won Jong Kim, Pohang-si (KR); Ji Hyun Lee, Busan (KR)

(73) Assignee: POSTECH ACADEMY—INDUSTRY FOUNDATION, Pohang-si (KR)

( * ) Notice: Subject to any disclaimer, the term of this patent is extended or adjusted under 35 U.S.C. 154(b) by 2 days.

(21) Appl. No.: 16/963,315

(22) PCT Filed: Apr. 13, 2018

(86) PCT No.: PCT/KR2018/004326
§ 371 (c)(1),
(2) Date: Jul. 20, 2020

(87) PCT Pub. No.: WO2019/189979
PCT Pub. Date: Oct. 3, 2019

(65) Prior Publication Data
US 2021/0371863 A1    Dec. 2, 2021

(30) Foreign Application Priority Data

Mar. 28, 2018  (KR) .................. 10-2018-0035864

(51) Int. Cl.
*C12N 15/115*  (2010.01)
*A61K 31/713*  (2006.01)
*C12Q 1/6886*  (2018.01)

(52) U.S. Cl.
CPC .......... *C12N 15/115* (2013.01); *A61K 31/713* (2013.01); *C12Q 1/6886* (2013.01); *C12N 2310/16* (2013.01); *C12N 2310/3519* (2013.01); *C12N 2310/52* (2013.01)

(58) Field of Classification Search
CPC . C12N 15/115; C12N 2310/16; A61K 31/713
See application file for complete search history.

(56) References Cited

U.S. PATENT DOCUMENTS

| 2003/0032785 A1* | 2/2003 | Gold ................. C12N 15/115 536/23.1 |
| 2010/0183634 A1* | 7/2010 | Luo .................. C12Q 1/6811 435/6.12 |
| 2012/0142013 A1 | 6/2012 | Lee et al. |
| 2015/0119254 A1 | 4/2015 | Riken et al. |
| 2021/0230601 A1* | 7/2021 | Yan .................. C12N 15/11 |

FOREIGN PATENT DOCUMENTS

| KR | 10-1759209 | 7/2011 |
| KR | 10-1189790 | 10/2012 |
| KR | 10-2014-0091750 | 7/2014 |
| KR | 10-2016-0101260 | 8/2016 |
| KR | 10-1726213 | 4/2017 |
| KR | 10-2019407 | 5/2018 |

OTHER PUBLICATIONS

PCT/KR2018/004326, Written opinion of the International Search Authority, English translation pp. 1-7 (Year: 2018).*
Pooja Dua et al.,"Patents on SELEX and Therapeutic Aptamers", Recent Patents on DNA & Gene Sequences 2008, vol. 2, No. 3, 172-186, Feb. 2008.
Jingjing Li, et al, "Y-Shaped DNA Duplex Structure-Triggered Gold Nanoparticle Dimers for Ultrasensitive Colorimetric Detection of Nucleic Acid With The Dark-Field Microscope", Analytical Chemistry 89(23), 12850-12856, Nov. 9, 2017.
Dausse E. et al., "Aptamers: a new class of oligonucleotides in the drug discovery pipeline?", Current Opinion in Pharmacology 2009, 9:602-607, Aug. 29, 2009.
Collins ML, et al, "A branched DNA signal amplification assay for quantification of nucleic acid targets below 100 molecules/ml", Nucleic Acids Research, 1997, vol. 25, No. 15 2979-2984, Aug. 1997.
Kern D, et al, "An Enhanced-Sensitivity Branched-DNA Assay for Quantification of Human Immunodeficiency Virus Type 1 RNA in Plasma", Journal of Clinical Microbiology, p. 3196-3202 Dec. 1996.
Cardones, A. R. et al., "VEGF Inhibitors in Cancer Therapy", Current pharmaceutical design 2006, 12, 387-394 , 2006.
Vasudev, N. S. et al., "Anti-angiogenic Therapy for Cancer: Current Progress, Unresolved Questions and Future Directions", Angiogenesis 2014, 17, 471-494, Jul. 2014.
Kamba, T. et al., "Mechanisms of adverse effects of anti-VEGF therapy for cancer", British Journal of Cancer 2007, 96, 1788-1795, May 22, 2007.
Al-Husein, B. et al., "Antiangiogenic Therapy for Cancer: An Update", The Journal of Human Pharmacology and Drug Therapy 2012, 32(12), 1095-1111, Dec. 2012.
Gragoudas, E. S. et al., "Pegaptanib for Neovascular Age-Related Macular Degeneration", The New England journal of medicine 2004, 351, 2805-2816, Dec. 30, 2004.
Schmidt-Erfurth, U. et al., "Guidelines for the management of neovascular age-related macular degeneration by the European Society of Retina Specialists (EURETINA)", The British journal of ophthalmology 2014, 98, 1144-1167, Sep. 2014.
Tucker, C. E. et al., "Detection and plasma pharmacokinetics of an anti-vascular endothelial growth factor oligonucleotide-aptamer (NX1838) in rhesus monkeys", Journal of Chromatography B, 732 (1999) 203-212, Sep. 1999.

(Continued)

*Primary Examiner* — Brian Whiteman
(74) *Attorney, Agent, or Firm* — Lex IP Meister, PLLC (57) ABSTRACT

The present invention relates to a highly efficient aptamer complex comprising a branched DNA and an aptamer, and a pharmaceutical use thereof. More specifically, the aptamer complex of the present invention relates to a highly efficient aptamer complex including a Y-shaped DNA as the branched DNA and using vascular endothelial growth factor (VEGF) as a target molecule. The aptamer complex of the present invention and a pharmaceutical composition comprising the same as an active ingredient are expected to be widely used in the medical field since the binding efficiency with the target molecule is more remarkable than that of the conventional aptamer.

7 Claims, 8 Drawing Sheets

Specification includes a Sequence Listing.

(56) References Cited

OTHER PUBLICATIONS

Hong-Min Meng, et al, "Aptamer-integrated DNA nanostructures for biosensing, bioimaging and cancer therapy", Chem. Soc. Rev., 2016, 45, 2583-2602, Mar. 2016.

Sena Cansiz, et al, "DNA Aptamer Based Nanodrugs: Molecular Engineering for Efficiency", Chem. Asian J. 2015, 10, 2084-2094, Sep. 2015.

Cuichen Wu, et al, 'Building a Multifunctional Aptamer-Based DNA Nanoassembly for Targeted Cancer Therapy', J. Am. Chem. Soc. 2013, 135, 18644-18650, Nov. 18, 2013.

Kyung Soo Park, et al, 'Predictive Evaluation for the Preparation of a Synthetic Y-shaped DNA Nanostructure', Biotechnology and Bioprocess Engineering 19: 262-268, (2014).

Jihyun Lee, et al., "Self-Assembled Aptamer Nanoconstruct: A Highly Effective Molecule-Capturing Platform Having Therapeutic Applications", Advv Therap. 2019, 2, 1800111.

\* cited by examiner

HIGH EFFICIENCY APTAMER COMPLEX COMPRISING BRANCHED DNA AND APTAMER, AND USE THEREOF

TECHNICAL FIELD

This application claims the benefit of priority based on Korean Patent Application No. 10-2018-0035864 filed on Mar. 28, 2018, and the entire contents of which are incorporated herein by reference.

The present invention relates to a highly efficient aptamer complex comprising a branched DNA and an aptamer and a pharmaceutical use thereof. More specifically, the aptamer complex of the present invention relates to a highly efficient aptamer complex including a Y-shaped DNA as the branched DNA and using vascular endothelial growth factor (VEGF) as a target molecule.

BACKGROUND ART

Ligand materials having high affinity with cancer cell surface proteins and capable of specifically binding to cancer cells are important for cancer diagnosis and development of therapeutic agents. These ligand materials may also be used as cancer biomarkers, and understanding of biomarkers may promote the development of new cancer therapeutic agent. Aptamers are single-stranded DNA or RNA oligonucleotides that may be folded into a specific three-dimensional structure to bind with high affinity and specificity to the target. Targets for aptamers may be small molecule compounds, peptides, or proteins, or may be the cells themselves (Dua, P. et al., RecentPat. DNA GeneSeq., 2: 172, 2008). These aptamers have advantages such as smaller size, better tissue permeability, ease of chemical manipulation, and no immune response, compared to antibodies. In addition, when applied to in vivo imaging, the aptamer has a faster response rate and a better signal-noise ratio due to its small size compared to antibodies. Aptamers may also be attached to the surface of magnetic nanoparticles to be used in magnetic resonance imaging (MRI) in order to improve image specificity. As a cancer therapeutic agent, aptamers may be used as "escort aptamers" that directly inhibit signaling pathways for cancer growth by blocking cancer growth factors or growth factor receptors, or transport therapeutic molecules such as cytotoxic agents or siRNA to target cells. Accordingly, specific aptamers targeting cancer cell types or cancer cell surface proteins have been developed as novel cancer diagnostic and therapeutic agents. For example, Korean Patent No. 10-1759209 discloses a nucleic acid aptamer capable of specifically binding to a breast cancer cell or tissue, and Korean Patent No. 10-1189790 discloses a nucleic acid aptamer capable of specifically binding to a pancreatic cancer cell or tissue. However, conventional aptamer for cancer treatment is likely to induce toxicity due to a large amount of non-specific accumulation when injected along a blood vessel, and the effect of suppressing the growth of cancer cells in the body is less than expected, and thus, there are many limitations in practical clinical applications.

On the other hand, a branched DNA is a DNA in which artificial branching occurs in the DNA helix structure, and typically includes a Y-shaped DNA or an X-shaped DNA, and the case where three types of nucleic acid sequences are combined is called a Y-shape and the case where four types of nucleic acid sequences are combined is called an X-shape (Jingjing Li, et al., Anal. Chem., 2017, 89(23), pp 12850-12856).

The present invention relates to a highly efficient aptamer complex comprising a branched DNA and an aptamer, and the aptamer complex of the present invention and the pharmaceutical composition comprising the same as an active ingredient are expected to be widely used in the medical field since the binding efficiency with the target molecule is remarkably excellent compared to that of the conventional aptamer.

PRIOR ART DOCUMENTS

Patent Documents

Korean Patent No. KR10-1759209
Korean Patent No. KR10-1189790

DISCLOSURE

Technical Problem

It is an object of the present invention to provide a highly efficient aptamer complex comprising a branched DNA and an aptamer, and a pharmaceutical composition for treating a cancer, comprising the same as an active ingredient. However, the technical problem to be achieved by the present invention is not limited to the above-mentioned problems, and other problems that are not mentioned will be clearly understood by those skilled in the art from the following description.

Technical Solution

Hereinafter, various embodiments described herein will be described with reference to the drawings. In the following description, various specific details such as specific forms, compositions, processes, and the like will be described in order to fully understand the present invention. However, certain embodiments may be practiced without one or more of these specific details, or in combination with other known methods and forms. In other instances, well-known processes and manufacturing techniques will be not described in specific details in order not to unnecessarily obscure the present invention. Reference throughout the present specification to "one embodiment" or "an embodiment" means that a particular feature, form, composition or property described in connection with the embodiment is included in one or more embodiments of the invention. Thus, the context of "in one embodiment" or "an embodiment" expressed in various positions throughout the present specification does not necessarily represent the same embodiment of the invention. Additionally, particular features, forms, compositions, or properties may be combined in any suitable way in one or more embodiments.

In the present specification, an "aptamer" is a 15-40 single-stranded oligonucleotide that forms a specific three-dimensional structure, and has a stem loop structure and a property that specifically binds to a specific molecule. The aptamer is easy to chemically synthesize and is a compound that is easy to modify chemically, is stable to heat, and has very high specificity for a target. The sequence of the aptamer may be discovered by a method called selective evolution of ligands by exponential enrichment (SELEX), and hundreds of aptamer sequences have already been disclosed. The aptamer is often compared to an antibody in that it specifically binds to a target, but has no immune response. Many aptamers that may bind to various target molecules, including small molecule organic materials, peptides, and membrane proteins, have been continuously discovered. The aptamer is often compared to a single antibody because of its characteristic that it may bind to a target molecule with unique high affinity (usually pM level) and specificity, and is especially called a "chemical antibody", and thus, the potential as an alternative antibody is also very high.

The antibody is difficult to produce and is not easy to modify due to a large molecular structure (~150 kDa), whereas the aptamer is a small molecular structure composed of nucleic acids of about 20 to 60 mer in length and has the advantage of facilitating various necessary modifications. The aptamer has a very high stability compared to the antibody. Protein or antibody drugs cannot be stored or transported at room temperature, but the aptamer is possible, can maintain its function even after sterilization, and can be regenerated again in a short time even when it is denatured, and thus, it is very easy to apply for diagnostics, which requires long time and repeated use.

Looking at the process of discovering new aptamers through SELEX, first, (i) in the case of DNA synthesis and RNA, nucleic acid libraries having various forms are prepared using an in vitro transcription method. (ii) Just as the antibody binds to various kinds of antigens, the various nucleic acid constructs (aptamer candidate molecules) in the nucleic acid construct library have the ability to bind to various target materials, and thus, the process of selecting only a nucleic acid construct capable of binding to a desired target molecule is carried out in the next process. (iii) Through a method such as affinity chromatography, the non-bound nucleic acid constructs are removed and only those binding to the target molecule can be selectively obtained. (iv) Finally, after the nucleic acid constructs are eluted from the target molecules and the nucleic acids are amplified, aptamers showing very excellent binding and specificity can be discovered by repeating these processes again 5 to 15 more times using the obtained nucleic acid constructs. As described above, the initial aptamers obtained through SELEX also undergo a post-SELEX process to improve to more stable and powerful aptamers. A typical example is to replace the ribose 2'-OH of the RNA aptamer with a 2'-F, 2'-$NH_2$, or 2'-O-methyl group. If such a modification is carried out, it is possible to obtain an aptamer having an excellent resistance to a nucleic acid degrading enzyme and an increase in stability in blood of more than 10,000 times. In addition, it is possible to reduce the rapid extinction in the blood by conjugating the aptamer to a polymer such as polyethylene glycol (PEG), or diacylglycerol or cholesterol. In addition, it may be used in the biosensor/chip field by preparing an aptamer having biotin bound to a 5'-end or 3'-end and attaching it to a streptavidin support (Dausse E. et al., Aptamers: a new class of oligonucleotides in the drug discovery pipeline, Curr. Opin. Pharmacol, 2009).

Under this technical background, DNA constructs developed using DNA are self-assembled by sequence-specific interactions between complementary nucleic acids, and the DNA constructs, which are self-assembled nano-unit constructs, induce dynamic movements by controlling the base sequence and inducing structural transformation by changes in the surrounding environment such as pH, temperature, and light. Although many studies have been conducted on DNA-conjugated nanoparticles, there is a lot of non-specific accumulation when injected along blood vessels, which may cause toxicity, and thus, there is a need for research on a system for delivering drug substances targeting only cancer cells.

In the present invention, a "branched DNA (bDNA)" is DNA in which artificial branching occurs in the DNA helix structure, and typically includes a Y-shaped DNA or an X-shaped DNA, and the case where three types of nucleic acid sequences are combined is called a Y-shape and the case where four types of nucleic acid sequences are combined is called an X-shape (Jingjing Li, et al., Anal. Chem., 2017, 89(23), pp 12850-12856). The branched DNA is effective for reliable quantitative analysis of nucleic acid molecules, or highly efficient binding with target molecules. The branched DNA is very stable against nucleic acid amplification such as PCR, and non-specific hybridization, and thus, it is possible to lower the quantitative detection limit using conventional nucleic acids to about 50 molecules (Collins M L, et al., Nucleic Acids Res. 1997 Aug. 1; 25(15): 2979-84; and Kern D, et al., J. Clin Microbiol. 1996 December; 34(12): 3196-202).

In the present specification, "vascular endothelial growth factor (VEGF)" is an important survival factor of vascular endothelial cells. In terms of biological function, VEGF is one of the most potent angiogenic factors and an important regulator of vascular permeability. VEGF has been widely accepted as a major regulator of wet-type age-related macular degeneration (AMD) and pathological angiogenesis-related diseases such as angiogenic tumor growth. In addition, as a potent enhancer of vascular permeability, it is also deeply involved in diseases associated with pathogenic vascular leakage, including diabetic macular edema.

Treatment of anti-VEGF is considered as the most important treatment method for wet-type AMD, diabetic macular edema, and cancer. There are various techniques for blocking the VEGF pathway using (1) antibody (bevacizumab, ranibizumab) or (2) aptamer (pegaptanib) for neutralizing VEGF or VEGF receptor (VEGFR), (3) siRNA for targeting VEGF mRNA, (4) small molecule tyrosine kinase inhibitor (lapatinib, sunitinib) for VEGF receptor, and (5) soluble VEGF receptor (sVEGFR) that inhibits the interaction between VEGF and VEGFR (Cardones, A. R. et al., Current pharmaceutical design 2006, 12, 387-394; and Vasudev, N. S. et al., Angiogenesis 2014, 17, 471-494).

Recently, many anti-VEGF drugs have been reported for use in the treatment of VEGF-related diseases. However, there is a problem that the efficiency, toxicity, and stability of these drugs in the body under physiological conditions are uncertain (Kamba, T. et al., British Journal of Cancer 2007, 96, 1788-1795; and Al-Husein, B. et al., Pharmacotherapy: The Journal of Human Pharmacology and Drug Therapy 2012, 32, 1095-1111).

Pegaptanib, which is an RNA aptamer for VEGF165, was first approved by the FDA as an anti-VEGF drug for the treatment of neovascular AMD. This aptamer drug is safe, but not very efficient compared to other alternative anti-VEGF drugs, such as ranibizumab, which is an anti-VEGF monoclonal antibody, and aflibercept, which is VEGF receptors 1 and 2 fused to the Fc portion of IgG, and thus, it is rarely used in clinical practice (Gragoudas, E. S. et al., The New England journal of medicine 2004, 351, 2805-2816; and Schmidt-Erfurth, U. et al., The British journal of ophthalmology 2014, 98, 1144-1167). Binding affinity to VEGF and in vivo stability are major factors affecting the biological effects of anti-VEGF aptamers. Although pegaptanib is structurally modified to improve resistance to nuclease, it has a problem that the in vivo half-life is 9.3 hours after intravenous injection and 12 hours after subcutaneous injection, which are relatively short (Tucker, C. E. et al., Journal of chromatography. B, Biomedical sciences and applications 1999, 732, 203-212).

In the present specification, an "aptamer complex" is the aptamer complex developed in the present invention and means an aptamer comprising a branched DNA, an aptamer corresponding to a target sequence, and a terminal DNA. Although not limited thereto, the branched DNA is preferably a Y-shaped DNA, the target sequence is preferably a sequence corresponding to a vascular endothelial growth factor (VEGF) protein, and the terminal DNA is preferably Blu_end.

Angiogenesis is very important for the growth and metastasis of solid tumors. In particular, tumor angiogenesis and angioplasia, which are very related to the VEGF signaling pathway, are important processes for tumor onset. So far, there have been many reports of anti-cancer treatment using anti-VEGF factor as "anti-VEGF therapy" or "anti-angiogenic therapy." Previous studies by the present inventors disclosed a polymer-amplified VEGF aptamer, but a complex having a highly entangled structure by the RCA process, such as AA, showed significantly lower VEGF capture efficiency compared to the same amount of oligomeric aptamer. From this point of view, the aptamer complex comprising the branched DNA, the aptamer corresponding to the target sequence, and the terminal DNA has high stability and capture efficiency as an aptamer complex therapeutic agent for suppressing tumor growth in vivo, and thus, it is expected to be widely used in clinical practice.

In the present invention, the target molecule may be any one selected from the group consisting of vascular endothelial growth factor (VEGF), bovine serum albumin (BSA), adenosine triphosphate (ATP), hepatitis C virus (HCV), and human immunodeficiency virus (HIV), and any target material for which a DNA-based aptamer has been developed may be used. That is, if a material other than VEGF is also designed to correspond only to the aptamer sequence, any material may be selected and captured. For example, aptamers for BSA may be specified to form aptamer complexes with branched DNA, thereby capturing only BSA.

In the present invention, in preparing the highly efficient aptamer complex comprising the branched DNA to selectively and efficiently capture a specific target molecule, an vascular endothelial cell growth factor commonly found around cancer as a specific target protein and known as a causative agent of macular edema may be set, and thus, it is preferably possible to to select and use an vascular endothelial cell growth factor, but is not limited thereto.

In the present invention, a "pharmaceutical composition" means a composition to be administered for a specific purpose. For the purpose of the present invention, the pharmaceutical composition of the present invention is intended to be used for the treatment of cancer or macular edema, and is a composition comprising a highly efficient aptamer complex comprising a branched DNA and an aptamer as active ingredients and may comprise a protein involved therein and a pharmaceutically acceptable carrier, excipient, or diluent.

The "pharmaceutically acceptable" carrier or excipient means one approved by the government, or one listed in the pharmacopeia or other generally recognized pharmacopeia for use in vertebral animals, and more particularly in humans.

For parenteral administration, the pharmaceutical compositions of the present invention may be in the form of suspensions, solutions, or emulsions, in oily or aqueous carriers, and may be prepared in the form of solid or semi-solid. In addition, the pharmaceutical composition of the present invention may comprise formulating agents such as a suspending agent, a stabilizing agent, a solubilizing agent, and/or a dispersing agent, and may be sterilized. The pharmaceutical composition may be stable under the conditions of manufacture and storage, and may be preserved against the contaminating action of microorganisms such as bacteria and fungi. Alternatively, the pharmaceutical composition of the present invention may be in sterile powder form for reconstitution with a suitable carrier prior to use. The pharmaceutical composition may be present in unit-dose form, in microneedle patch, in ampoule or in other unit-dose container, or in multi-dose containers. Alternatively, the pharmaceutical composition may be stored in a freeze-dried (lyophilized) state requiring only the addition of a sterile liquid carrier, for example, water for injection immediately prior to use. An immediate injectable solution and suspension may be prepared as a sterile powder, granule, or tablet.

In some non-limiting embodiments, the pharmaceutical composition of the present invention may be formulated or included in the form of microspheres in a liquid. In some non-limiting embodiments, the pharmaceutical composition of the present invention may comprise pharmaceutically acceptable compounds and/or mixtures thereof at concentrations between 0.001 and 100,000 U/kg. In addition, in some non-limiting embodiments, the excipient that is suitable for the pharmaceutical composition of the present invention may include a preservative, a suspending agent, an additional stabilizer, a dye, a buffering agent, an antibacterial agent, an antifungal agent, and an isotonic agent, for example, a sugar or sodium chloride. As used herein, the term "stabilizer" refers to a compound that is selectively used in the pharmaceutical composition of the present invention to increase shelf life. In a non-limiting implementation, the stabilizer may be a sugar, an amino acid, or a polymer. In addition, the pharmaceutical composition of the present invention may comprise one or more pharmaceutically acceptable carriers, and the carrier may be a solvent or a dispersion medium. Non-limiting examples of the pharmaceutically acceptable carrier include water, saline, ethanol, polyols (for example, glycerol, propylene glycol, and liquid polyethylene glycol), oils, and suitable mixtures thereof. Non-limiting examples of sterilization techniques that are applied to the pharmaceutical composition of the present invention include filtration through a bacterial-restraining filter, terminal sterilization, incorporation of sterile agents, radiation, sterilization gas irradiation, heating, vacuum drying, and freeze drying.

As used herein, "administration" means introducing the composition of the present invention into a patient by any suitable method, and the composition of the present invention may be administered through any general route, as long as it can reach a target tissue. Oral administration, intraperitoneal administration, intravenous administration, intramuscular administration, subcutaneous administration, intradermal administration, intranasal administration, intrapulmonary administration, intrarectal administration, intracavitary administration, intraperitoneal administration, or intrathecal administration may be made, and, for the purpose of the present invention, it is preferably administered in the form of an injection, but is not limited thereto.

The treatment method of the present invention may comprise administering a pharmaceutically effective amount of the pharmaceutical composition. In the present invention, the effective amount may be regulated depending on various factors, including the kind of disease, the severity of the disease, the kind and content of the active ingredients and other ingredients contained in the composition, the kind of formulation and the patient's age, body weight, general health condition, sex and diet, the time of administration, the route of administration, and the secretion rate of the composition, the duration of treatment, and drugs that are simultaneously used.

In one embodiment of the present invention, an aptamer complex comprising a branched DNA, an aptamer corresponding to a target sequence, and a terminal DNA is provided; the aptamer complex wherein the branched DNA is a Y-shaped DNA is provided; the aptamer complex wherein the Y-shaped DNA is any one or more selected from the group consisting of SEQ ID NOs: 1 to 6 is provided; the aptamer complex wherein the protein corresponding to the target sequence is any one or more selected from the group consisting of vascular endothelial growth factor (VEGF), bovine serum albumin (BSA), adenosine triphosphate (ATP), hepatitis C virus (HCV), and human immunodeficiency virus (HIV) is provided; the aptamer complex wherein the aptamer corresponding to the target sequence is any one or more selected from the group consisting of SEQ ID NOs: 7 to 9 is provided; and the aptamer complex wherein the terminal DNA is any one or more selected from the group consisting of SEQ ID NOs: 13 and 14 is provided.

In another embodiment of the present invention, a drug delivery system comprising the aptamer complex as an active ingredient is provided.

In another embodiment of the present invention, a pharmaceutical composition for treating an cancer, comprising the aptamer complex as an active ingredient is provided; and the pharmaceutical composition for treating an cancer, wherein the cancer is any one or more selected from the group consisting of melanoma, small cell lung cancer, non-small cell lung cancer, brain tumor, liver cancer, thyroid tumor, gastric cancer, prostate cancer, breast cancer, ovarian cancer, bladder cancer, lung cancer, colorectal cancer, breast cancer, prostate cancer, glioblastoma, cervical cancer, endometrial cancer, kidney cancer, colon cancer, pancreatic cancer, esophageal carcinoma, head and neck tumor, mesothelioma, sarcoma, cholangioma, small intestine adenocarcinoma, childhood malignant cancer, and epidermal cancer, is provided.

In another embodiment of the present invention, a kit for diagnosing a cancer, comprising the aptamer complex as an active ingredient is provided.

Hereinafter, the present invention will be described in detail step by step.

Advantageous Effects

The present invention relates to a highly efficient aptamer complex comprising a branched DNA and an aptamer, and the use thereof, and the aptamer complex of the present invention uses the branched DNA that is very stable against nucleic acid amplification and non-specific hybridization, and thus, the binding efficiency with the target molecule is more remarkably excellent than that of the conventional aptamer. In addition, the pharmaceutical composition comprising the aptamer complex of the present invention as the active ingredient has no risk of toxicity in vivo, is stable in the blood, and has excellent therapeutic effects on target diseases, and thus, it is expected to be widely used in the medical field.

DESCRIPTION OF DRAWINGS

FIG. 7A shows a representative X-ray scattering profile of the DNA complex, and FIG. 7B shows the Guinier transform values, and FIG. 7C shows the Kratky expression graph.

BEST MODE

Hereinafter, the present invention will be described in more detail through examples. It will be apparent to those skilled in the art that these examples are only for illustrate the present invention in more detail and the scope of the present invention is not limited to these examples in accordance with the gist of the present invention.

Example 1: Preparation and Physical Analysis of Target Molecular Capture Construct

Example 1-1. Preparation of Constructed Aptamer (CA) Complex

Figure 1:
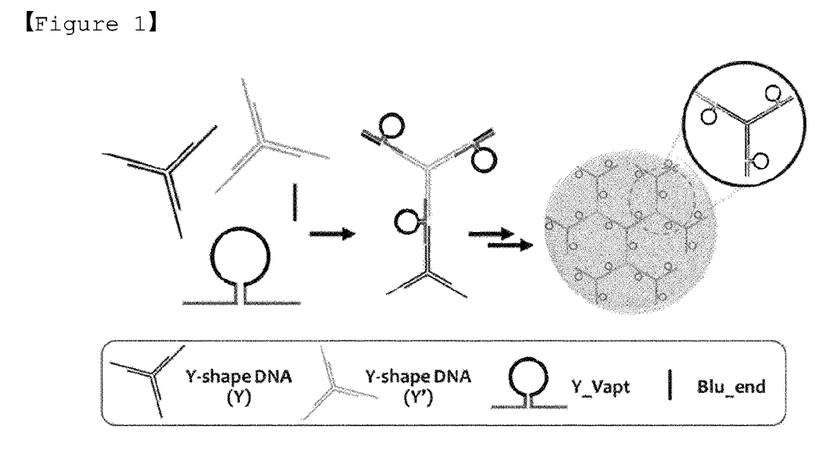
FIG. 1 is a drawing showing a schematic view of manufacturing the CA designed in the present invention, according to an embodiment of the present invention.

In this study, a target molecular capture platform was designed using a "constructed aptamer (CA) complex," which is an aptamer complex based on a Y-shaped DNA structure. The basic structure of the CA is composed of (1) two Y-shaped DNAs (Y-5, Y-3), which are the framework of the entire structure, (2) Y_Vapt, which is a aptamer capable of hybridizing with a Y-shaped DNA protrusion, and (3) Blu_end as DNA for blunt end formation. The Blu_end is a kind of terminal DNA, and was used to block the overhang (a single strand from which unpaired nucleotides protrude) of the Y-shaped DNA. In the CA platform of the present invention, hybridized oligomer aptamers are used for specific interaction and capture with target molecules. A schematic view of the constructed aptamer complex is shown in FIG. 1.

In this example, to capture human VEGF (hVEGF) overexpressed at the tumor site, the CA was prepared into a hairpin structured hVEGF DNA aptamer (Y_Vapt). Specifically, 6 types of Y-shaped branched DNAs (Y01-5, Y02-5, Y03-5, Y01-3, Y02-3, Y03-3), Blu_end, and Y-Vapt were mixed in the correct amount and annealed under the conditions in Table 1. In the case of CA, the generation of the CA is determined according to the ratio between Blu_end DNA and Y-shaped DNA. When various amounts of Blu_end were used to prepare the CA, it was designated as CA_G # (# of generation). hVEGFaptamer was prepared in the same manner as known technology (Lee, J, et al., J. Chem. Mater. 2016, 28, 3961; and Potty, A, et al., Biopolymers 2009, 91, 145). The sequence information of each material is set forth in Table 2, and when there is a modification at the 5'-end, it is indicated in square brackets.

TABLE 1

| Order | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Temperature [° C.] | 95 | 85 | 80 | 75 | 70 | 65 | 60 | 55 | 50 | 45 | 40 | 30 | 20 | 4 |
| Time [min] | 5 | 0.5 | 0.5 | 0.5 | 0.5 | 0.5 | 0.5 | 0.5 | 0.5 | 0.5 | 0.5 | 0.5 | 0.5 | 5 |

TABLE 2

| SEQ ID NO | Designation | Sequence (5'-3') | bp |
|---|---|---|---|
| SEQ ID NO: 1 | Y01-5 | GCTCCTCGCCTGAAGCTCGATGAATAGCGGTCAGATCCGTACCTA | 45 |
| SEQ ID NO: 2 | Y02-5 | GCTCCTCGCCTGAAGCTTCGTTCGCAATACGACCGCTATTCATCG | 45 |
| SEQ ID NO: 3 | Y03-5 | GCTCCTCGCCTGAAGCTTAGGTACGGATCTGCGTATTGCGAACGA | 45 |
| SEQ ID NO: 4 | Y01-3 | ATCCATGCCTAGACTGGCGATAAGTAGCTGTCCGCTCCTCG | 41 |
| SEQ ID NO: 5 | Y02-3 | GCTACTTATCGCCAGCATAACGCTTGCTTGTCCGCTCCTCG | 41 |
| SEQ ID NO: 6 | Y03-3 | AGCAAGCGTTATGCGTCTAGGCATGGATTGTCCGCTCCTCG | 41 |
| SEQ ID NO: 7 | Y_Vapt | AGCTTCAGGCGAGGAGCCCACCCCGTCTTCCAGACAAGAGTGCAGGGGTGGCGAGGAGCGGACA | 64 |
| SEQ ID NO: 8 | Pri_Vapt | CCCGTCTTCCAGACAAGAGTGCAGGG | 26 |
| SEQ ID NO: 9 | Phos_Vapt | [Phos]TTTTTAAGCTTGTCCGCTCCTCGCCACCCCTGCACTCTTGTCTGGAAGACGGGGTGGGCTCCTCGCCTGAAGCTT | 75 |
| SEQ ID NO: 10 | Y_Sc | AGCTTCAGGCGAGGAGCCCACTATTATGGAACCGAATTTTGTTTCATGTGGCGAGGAGCGGACA | 64 |
| SEQ ID NO: 11 | Pri_Sc | TATTATGGAACCGAATTTTGTTTCAT | 26 |
| SEQ ID NO: 12 | Phos_Sc | [Phos]TTTTTAAGCTTGTCCGCTCCTCGCCACATGAAACAAAATTCGGTTCCATAATAGTGGGCTCCTCGCCTGAAGCTT | 75 |
| SEQ ID NO: 13 | Blu_end | TGTCCGCTCCTCG | 13 |
| SEQ ID NO: 14 | FAM_Blu_end | [FAM]TGTCCGCTCCTCG | 13 |

In Table 2 above, [Phos] indicated in the sequence indicates that the sequence is phosphorylated, and [FAM] indicates that a fluorescent substance is linked to the sequence.

Figure 2:
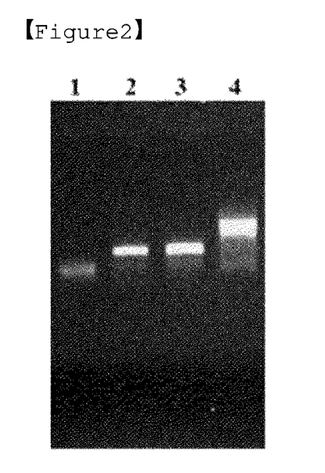
FIG. 2 is a drawing showing the results of confirming the generation and size of constructs of the CAs by electrophoresis, according to an embodiment of the present invention.

The prepared CA was stored at 4° C. until use and confirmed for the generation and size of the construct with polyacrylamide gel electrophoresis (PAGE 6%, stained with SYBR Gold®, 100 V for 45 minutes), and the results are shown in FIG. 2. In FIG. 2, the annealed product (line 4) moved less than Y-5 (line 2) and Y-3 (line 3), indicating that the molecular weight was greater.

As a control for the CA of the present invention, an oligomeric aptamer (OA) complex, an oligomeric scrambled DNA (OSc), an amplified aptamer (AA) complex, an amplified scrambled DNA (ASc), and a constructed scrambled DNA (CSc) were tested. For the OA, an oligomerichVEGFaptamer DNA was prepared by simple annealing. For the CSc, it was prepared by replacing Y_Vapt used for the preparation of CA with Y_Sc, and is a constructed scrambled DNA without VEGF capture ability, which corresponds to a control. The concentrations of aptamers in the OA, AA, and CA remained the same.

Example 1-2. Preparation of Amplified Aptamer (AA) Complex

According to CircLigase™ protocol, which is the well-known technique, cyclic DNA was obtained using Phos_Vapt and Phos_Sc as templates. More specifically, the phosphorylated modified DNA was mixed with ATP, $MgCl_2$, and ligase enzyme in a buffer, and reacted at 60° C. for 12 hours. After the enzyme inactivation process was carried out, the reaction was carried out for 30 minutes at 37° C. with 20 U of exonuclease I and 100 U of exonuclease III, and the enzyme inactivation process was carried out again. The synthesized cyclic DNA was purified by DNA PrepMate™-II, and then confirmed by polyacrylamide gel electrophoresis, and the concentration was measured by ultraviolet absorption at 280 nm.

A "rolling circle amplification (RCA)" process was carried out to prepare the amplified aptamer (AA) complex using the synthesized cyclic DNA, and then F29 polymerase protocol was carried out. Specifically, a buffer including dNTP, BSA, and F29 polymerase was added to the prepared cyclic Phos_Vapt and Pri_Vapt, and mixed well, and then the solution was sufficiently reacted at 30° C. Then, the solution was reacted at 80° C. to inactivate the enzyme, and then cooled slowly. The amplified aptamer complex using Phos_Sc and Pri_Sc was also prepared in the same manner.

Example 1-3. Dynamic Light Scattering (DLS) Analysis of Prepared Aptamers

Figure 3:
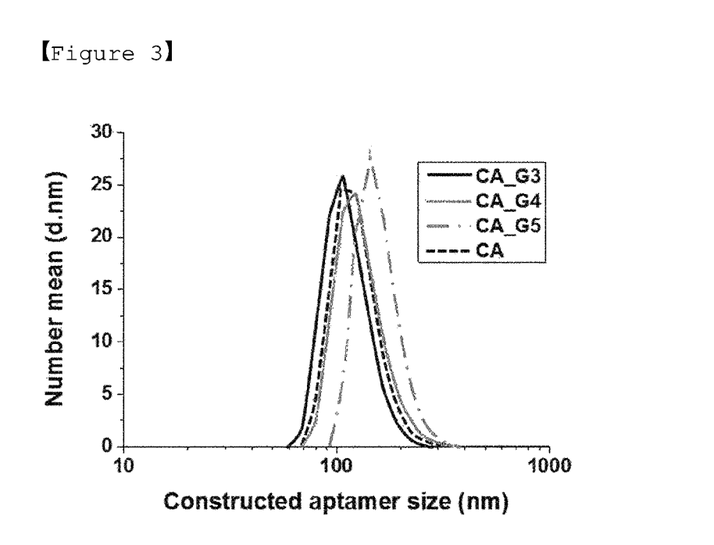
FIG. 3 is a drawing showing the results of a dynamic light scattering analysis of the CAs including various concentrations of Blu_end, according to an embodiment of the present invention.
Figure 4:
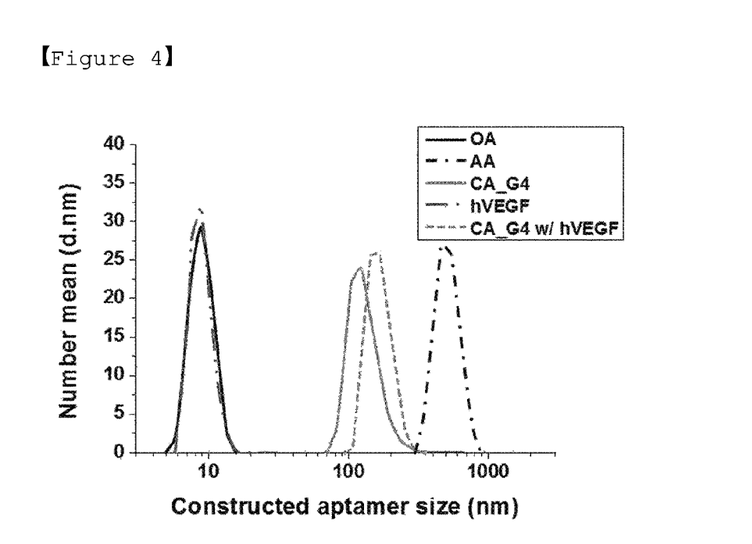
FIG. 4 is a drawing showing the results of a dynamic light scattering analysis of the OA, AA, and CA, according to an embodiment of the present invention.

Samples were prepared by a method of dissolving CA including 1 nmol OA, 10 pmol primer AA amplified for 4 hours, or 1 nmol aptamer in 50 mL of PBS. The size of each aptamer in the solution was measured using a Zetasizer Nano (Malvern Instruments, Malvern, UK). The measured results are shown in FIGS. 3 and 4. As a result of the experiment, the average diameters of the CA_G3, CA_G4, and CA_G5 were found to be 112.6 nm, 132.0 nm, and 159.4 nm, respectively, and the CA without Blu_end was found to be 123.5 nm. On the other hand, the diameters of the OA and AA were measured to be 8.9 nm and 510.0 nm, respectively, and it was found that the AA had a very large diameter compared to the CA.

Example 1-4. Image Analysis of Prepared Aptamers

Samples for transmission electron microscope (TEM) were prepared by a method of depositing 10 mM CA on a carbon grid coated with an ultrathin carbon film (400 mesh, Ted Pella, Redding, Calif., USA). The grid was dried for one day before measurement, and TEM images were obtained by JEM-1011 (JEOL, Tokyo, Japan).

Samples for atomic force microscope (AFM) were prepared by treating newly cut mica (Pelco Mica sheets, Ted Pella Corp.) with $NiCl_2$ and incubating for 10 minutes. The CA was dissolved in PBS including 10 mM $NiCl_2$, and the dissolved solution was deposited on the washed mica. After reaction for 30 minutes, the mica surface was washed with deionized water and dried. The dried samples were scanned in non-contact mode using VEECO Dimension 3100/Nanoscope V (VECCO).

Figure 5:
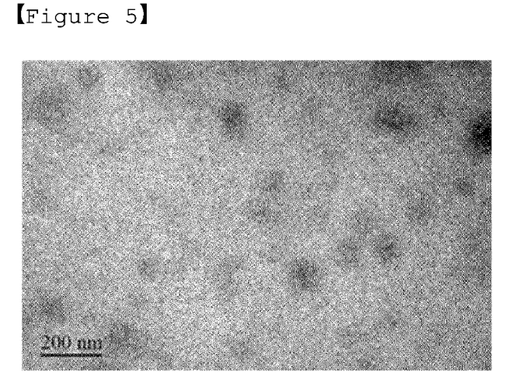
FIG. 5 is a drawing showing the results of a transmission electron microscope analysis of the CA, according to an embodiment of the present invention.
Figure 6:
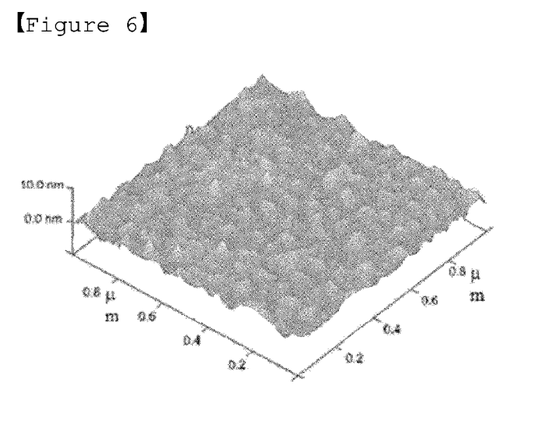
FIG. 6 is a drawing showing the results of an atomic force microscope analysis of the CA, according to an embodiment of the present invention.

The images obtained by measuring the CA (CA_G4) with the TEM and AFM are shown in FIGS. 5 and 6. As a result of the experiment, the spherical structure of the CA was confirmed, and the particle size was 105±9 nm.

Example 1-5. Synchrotron X-Ray Scattering Measurement of Prepared Aptamers

Figure 7:
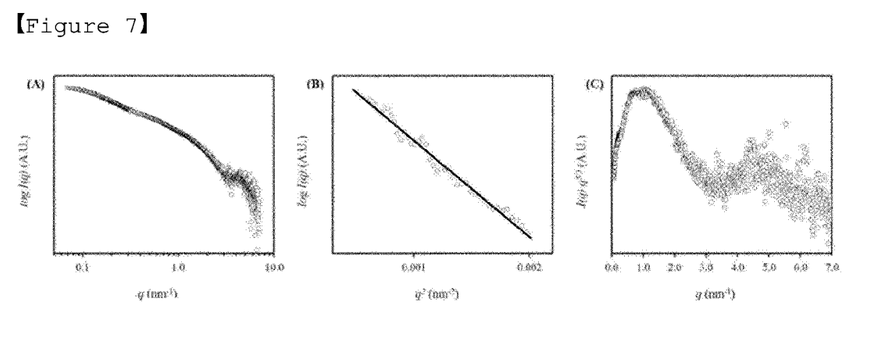
FIG. 7 is a drawing showing the results of a synchrotron X-ray scattering measurement of the CA, according to an embodiment of the present invention. More specifically.

Samples were prepared into 50 μL of PBS solution, and synchrotron X-ray scattering measurements were carried out on a 4C beamline. All samples were measured at 25° C. and sample-to-detector distances of 4 m and 1 m. Scattering data was collected through a two-dimensional charge-coupled detector (Model Rayonix 2D Mar, USA) using an X-ray radiation source of $\lambda=0.0756$ nm with an exposure time of 60 seconds, and the 2D scattering data was averaged circularly with respect to the beam center and normalized by monitoring the intensity of the X-ray beam transmitted through the scintilliation counter located at the back of the sample. Thereafter, the solvent scattering effect was removed from the scattering data by calculating the scattering intensity I (q) of the spherical particles in the solvent medium by an equation according to a known technique (Li, T, et al., Chem. Rev. 2016, online publishing) and treating it with the Guinier equation to extract the rotation radius (Rg) of the DNA complex (Guinier, A, et al., Wiley: New York, 1955). The results of the X-ray scattering measurements are shown in FIG. 7.

A representative X-ray scattering profile of the DNA complex is shown in FIG. 7A. In FIG. 7B, the maximum value of GuinierqRg was found to be 1.16 and the limit value of qRg was found to be 1.33. The generalized Kratky expression of X-ray data is shown in FIG. 7C, and it could be found that the local minimum value near q=0.34 nm does not reach zero. This is a characteristic of a spherical particle having a curved surface, and indicates that the prepared aptamer complex is a spherical object with an uneven surface.

Example 1-6. Confirmation of the Stability in Serum of Prepared Aptamers

Figure 8:
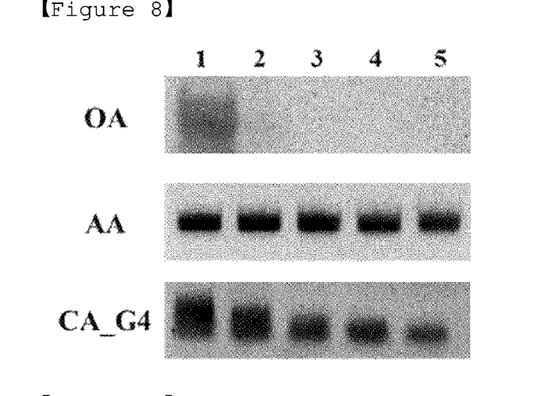
FIG. 8 is a drawing showing the results of confirming the stability in the serum of OA, AA, and CA, according to an embodiment of the present invention.

To confirm the stability of the low polymer aptamer complex (oligomeric aptamer; OA), amplified aptamer (AA) complex, and constructed aptamer (CA) complex to DNA nuclease in serum, the aptamer complexes were mixed in a 10% fetal bovine serum (FBS) solution and reacted for 3 days in a dark place at 37° C. The stability for the low polymer aptamer complex was analyzed by polyacrylamide gel electrophoresis, and the stability for the amplified aptamer complex and constructed aptamer complex was analyzed by agarose gel electrophoresis. The results are shown in FIG. 8. As a result of the experiment, it was observed that the OA was completely deteriorated after 12 hours, but the AA showed little progress of deterioration for 3 days. This indicates that the highly entangled structure of the AA is difficult to degrade by DNA nuclease, but the OA as a short DNA is easily degraded. For the CA_G4, it was found that its resistance to DNA nuclease was similar compared to that of the AA, but the degradation process was faster than the AA. From this, it could be found that the CA has an appropriate level of resistance to DNA nuclease.

Figure 9:
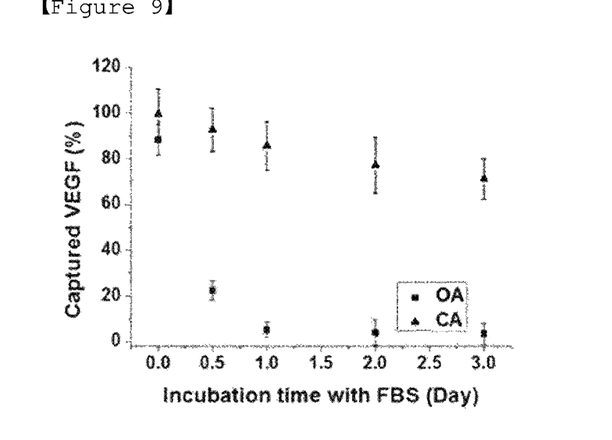
FIG. 9 is a drawing showing the results of measuring the hVEGF capture ability according to the degradation rate of the OA, AA, and CA as the kit, according to an embodiment of the present invention.

The hVEGF capture ability of the OA and CA_G4 according to the degradation rate is shown in FIG. 9. As a result of carrying out hVEGF capture experiments with samples incubated in serum for 0 hour (immediately after preparation), 12 hours, 1 day, 2 days, or 3 days, the capture efficiency of the CA_G4 was found to be 100% immediately after preparation, and the capture efficiency was found to be 71.7% when incubated for 3 days. However, the OA was shown to capture little hVEGF independent of serum incubation time. These results indicate that the ability of the CA_G4 to capture target molecules is fairly stable even in serum.

Example 2: Analysis of Biological Effects of Target Molecular Capture Constructs

Figure 10:
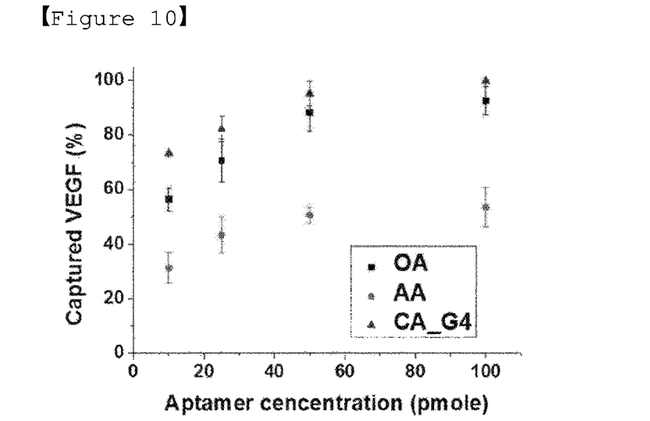
FIG. 10 is a drawing showing the results of measuring the hVEGF capture ability of the OA, AA, and CA by ELISA, according to an embodiment of the present invention.

Example 2-1. Confirmation of Capture Ability of OA, AA, and CA in hVEGF-Containing Solution To confirm the hVEGF capture ability of OA, AA, and CA, each prepared sample was mixed with hVEGF solution for 4 hours at room temperature, and the mixed solution was filtered through a PD-10 column (Sephadex G-25, GE Healthcare, Sweden). The amount of non-purified hVEGF was measured by the hVEGF enzyme-linked immunosorbent assay kit (ELISA kit, Komabiotech) according to the manufacturer's guidelines (absorbance measurement at 490 nm by VICTOR3 V™ (Multilabel Counter, Perkin Elmer, Wellesley, Mass., USA)). The hVEGF capture ability of other samples such as OSc, ASc, and CSc was measured in the same way, and the results are shown in FIG. 10.

As a result of the experiment, the OA and CA (CA_G4) had a remarkable capture efficiency, but the AA showed a relatively low capture efficiency. These results indicate that exposure of the reaction site of the DNA structure is very important to efficiently capture the target molecule. The overall structure of the CA is similar to that of the OA. However, the AA forms a highly entangled structure by the RCA process, so the target aptamer is not exposed to hVEGF, and thus, the interaction with the target molecule is low. The hVEGF capture efficiency of the CA was found to be saturated when the aptamer concentration reached 50 pmol (CA_G4=50 pmol aptamer).

Example 2-2. Confirmation of Cytotoxicity of Prepared Aptamer Complexes

Figure 11:
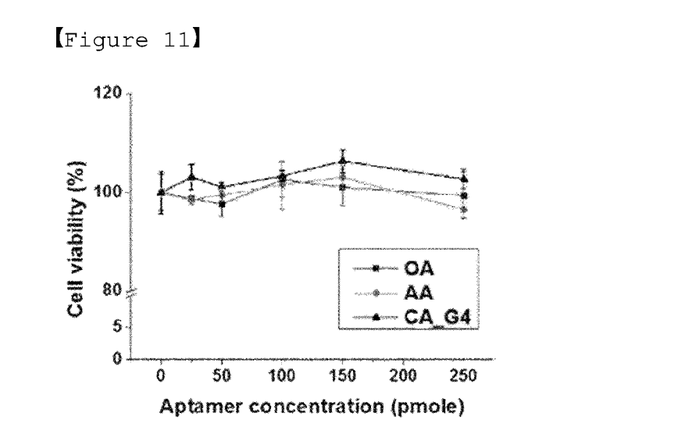
FIG. 11 is a drawing showing the results of measuring the cytotoxicity of the OA, AA, and CA by MTT, according to an embodiment of the present invention.

Cytotoxicity of each aptamer complex (OA, AA, and CA) was evaluated using standard MTT assay. First, A549 cells (lung adenocarcinoma cells) were seeded in 96-well plates at a density of $5 \times 10^3$ cells/well and incubated in a $CO_2$ incubator for 24 hours. The cells were treated with various concentrations (0, 250, 500, 1000, 1500, or 2500 nM) of OA, AA, or CA in serum-free medium (DMEM) for 6 hours, and the supernatant was removed and incubated in fresh serum-containing medium (DMEM) for 20 hours. Then, the mixture was replaced with fresh medium including MTT solution (5 mg/mL), and further reacted for 4 hours. The supernatant was removed and DMSO was added to each well to dissolve purple formazan crystals in the cells, and then absorbance was measured at 570 nm using a microplate spectrofluorometer (VICTOR3 V Multilabel Counter, Perkin Elmer, Wellesley, Mass., USA). The measured value was expressed as a relative percentage based on the measured value of the control sample added with medium only. The results of the MTT assay are shown in FIG. 11.

As a result of the experiment, the cell viability was not significantly reduced at an aptamer concentration of 0 to 250 pmol, and thus, all of the tested aptamer complexes were found to be biocompatible.

Figure 12:
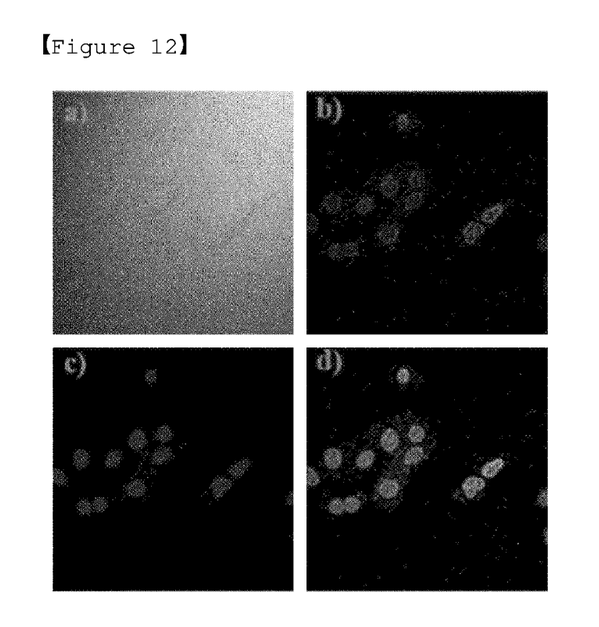
FIG. 12 is a drawing showing the results of evaluating the degree of cell uptake and internalization of the CA with the CA prepared with FAM fluorescently labeled Blu_end, according to an embodiment of the present invention.

Example 2-3. Confirmation of Degree of In Vitro Cell Uptake and Internalization To evaluate the degree of cell uptake and internalization of CA, CA manufactured with FAM fluorescently labeled Blu_end was prepared and treated with A549 cells. More specifically, A549 cells were seeded on a glass cover slip placed on a 12-well plate at a density of $2 \times 10^4$ cells/well and incubated for 18 hours. Thereafter, the culture broth (DMEM) was replaced with fresh serum-free DMEM containing FAM-labeled CA (containing 0.5 nmol FAM), and incubated for an additional 5 hours. After incubation, cold DPBS was added to block cell uptake, and the cells were washed and finally fixed at 4° C. overnight with 10% neutral buffered formalin (NBF). The cells on the cover slip were stained with DAPI and observed with a confocal laser scanning microscope (Modified Zeiss Axio Observer, Z1 epi-fluorescence microscope), and the image results are shown in FIG. 12.

As a result of the experiment, it was confirmed that the green fluorescence signal of the FAM-labeled CA was expressed in the nuclear region overlapping with the DAPI blue fluorescence, so that the cell internalization of the CA was smooth.

Example 2-4. Confirmation of In Vivo Cancer Treatment Effect of Prepared Aptamer Complexes All animal experiments in the present invention were carried out with the approval of the POSTECH Biotech Center Ethics Committee. First, A549 cells ($1 \times 10^8$) were subcutaneously inoculated into the flanks of each female BALB/c-nu/nu mouse, and then the mice were randomly divided into 5 groups (n=3), and OA, AA, CA, or CSc was administered by injection on days 1 and 5. The CSc has the same structure as the CA in vivo, but the DNA sequence is a different aptamer complex.

The anticancer effect of the administered aptamers on A549 cells was analyzed by measuring the tumor diameter with a caliper. The measured values were converted into tumor volumes using the equation described in Table 3 below.

TABLE 3

Tumor Volume = a × b² × 0.5
Wherein, a is a short dimension, and b is a long dimension.

After administration of each aptamer, tumor tracking and body weight change in mice were monitored until day 28, and the results are shown in FIGS. 13 to 16.

Figure 13:
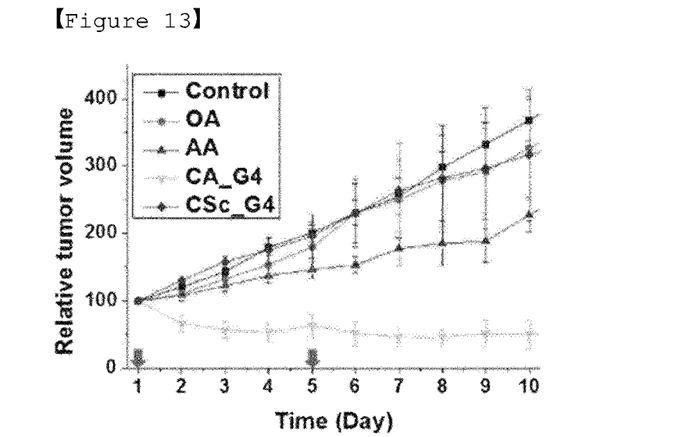
FIG. 13 is a drawing showing the results of tracking changes in tumor size in the short term after administration by the injection of the OA, AA, CA, or CSc into cancer cell-administered mice, according to an embodiment of the present invention.
Figure 14:
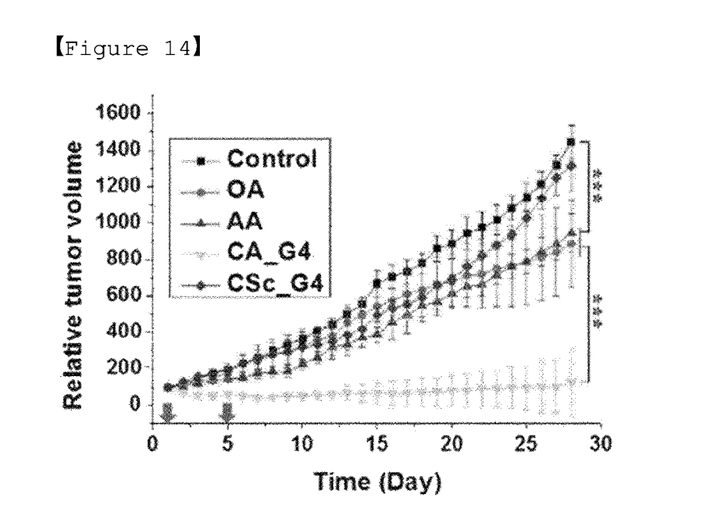
FIG. 14 is a drawing showing the results of tracking changes in tumor size in the long term after administration by the injection of the OA, AA, CA, or CSc into cancer cell-administered mice, according to an embodiment of the present invention.
Figure 15:
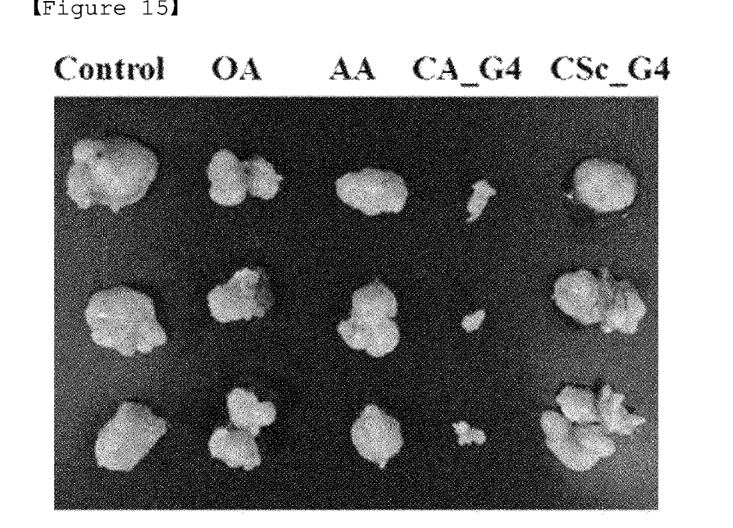
FIG. 15 is a drawing showing the overall shapes of the tumor tissues obtained on day 28 after administration by the injection of the OA, AA, CA, or CSc into cancer cell-administered mice, according to an embodiment of the present invention.

More specifically, FIGS. 13 and 14 show changes in tumor size. As a result of the experiment, it was found that the aptamer-untreated control increased the tumor size by 14.4 times on day 28, whereas the OA, AA, and CSc were increased by 8.9 times, 9.5 times, and 13.1 times, respectively. These are reduced levels compared to the aptamer-untreated control, but not significant levels with anti-tumor therapy. On the other hand, for the CA, it was found that the tumor was increased by 1.3 times on day 28, and thus, the tumor growth inhibitory effect was remarkable. The overall morphology of the tumor obtained on day 28 is shown in FIG. 15.

Figure 16:
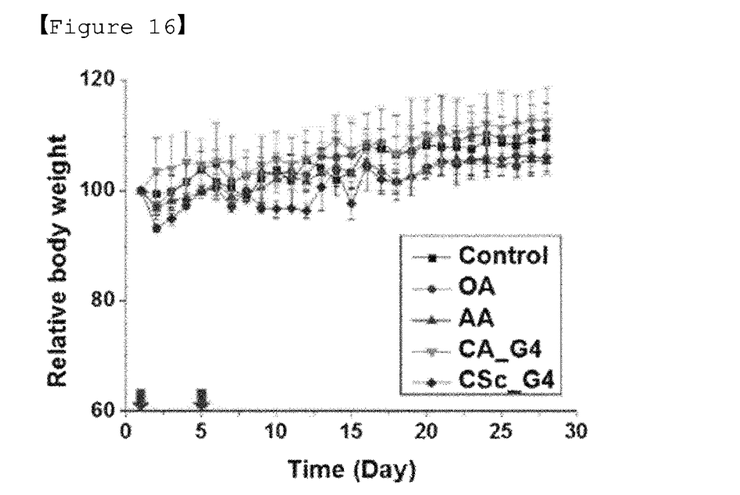
FIG. 16 is a drawing showing the results of tracking changes in body weight of mice in the long term after administration by the injection of the OA, AA, CA, or CSc into cancer cell-administered mice, according to an embodiment of the present invention.

The body weight change of the mice is shown in FIG. 16. There was no significant change in the body weight of the mice until day 28 in all tested groups. This indicates that the designed OA, AA, and CA are not toxic under biological conditions.

Example 2-5. Confirmation of Histological and Chemical Changes in Tumor Tissue For immunohistochemical analysis, each aptamer complex (OA, AA, CA, or CSc) was administered to tumor cell-injected mice, and then, the mice were sacrificed on day 4. Tumors were excised and fixed in 10% NBF for 24 hours, and then embedded with paraffin and sliced to a thickness of 4 mm using a Finesse ME microtome. To confirm histological changes of the tumor, tumor sections were stained with hematoxylin and eosin (H & E) and an ×10 magnification image was obtained with an optical microscope (Nikon eclipse 80i, USA).

In the case of immunohistochemical staining using CD-31 antibody, the sections sliced into a thickness of 4 mm were treated with a blocking solution (containing 5 w/v % BSA) for 15 minutes to prevent non-specific binding, washed several times with PBS, and treated with primary antibody for 1 hour at room temperature. Thereafter, these were treated with goat anti-rabbit IgG-FITC-labeled secondary antibody for 1 hour. Finally, the cover slip was mounted with a mounting medium including DAPI, and stored in a dark place at 4° C. Fluorescence images were obtained with a confocal laser scanning microscope (Modified Zeiss Axio Observer, Z1 epi-fluorescence microscope) at ×40 magnification.

Figure 17:
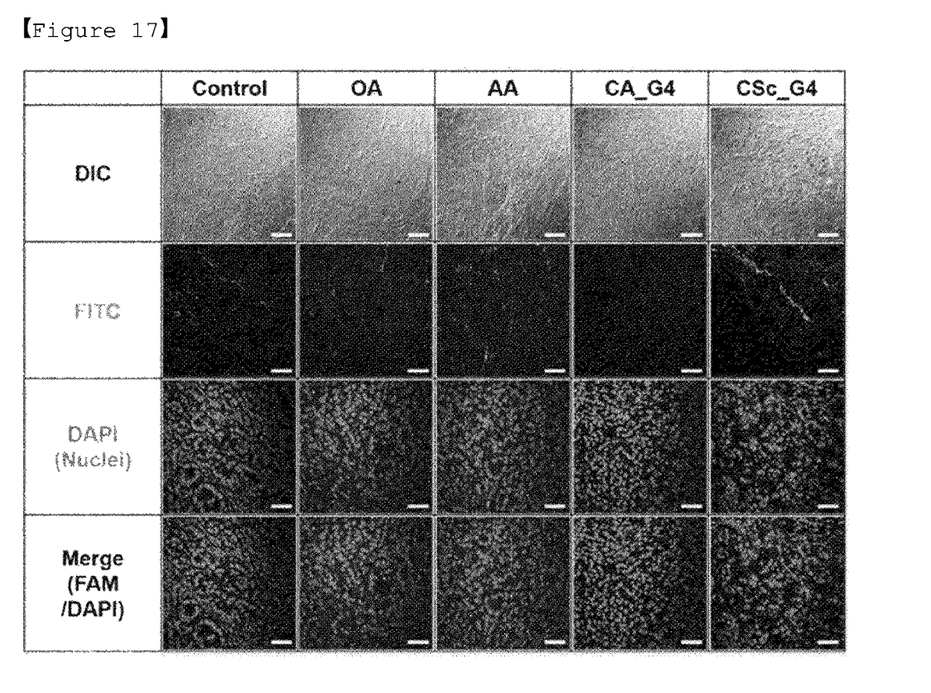
FIG. 17 is a drawing showing the results of CD-31 tumor marker staining on day 28 after administration by the injection of the OA, AA, CA, or CSc into cancer cell-administered mice, according to an embodiment of the present invention.
Figure 18:
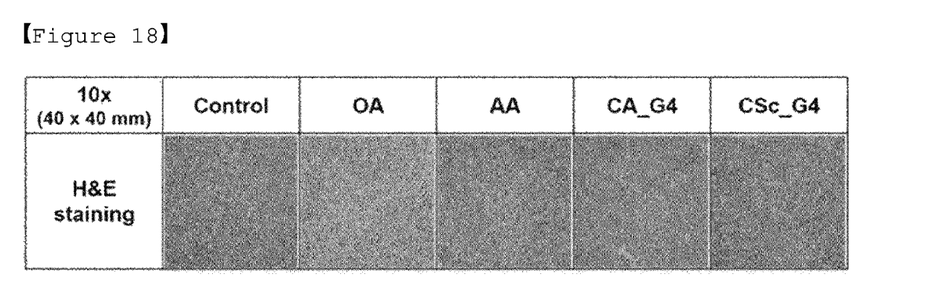
FIG. 18 is a drawing showing the results of H & E staining on day 28 after administration by the injection of the OA, AA, CA, or CSc into cancer cell-administered mice, according to an embodiment of the present invention.

The image results are shown in FIGS. 17 and 18. As a result of the experiment, tumor tissues were stained with CD-31 to express green fluorescence (FITC) in the aptamer-untreated control, OA, AA, and CSc, but green fluorescence was hardly expressed in the CA. Even in H&E staining, apoptosis and necrosis were clearly observed in the CA, but not significantly showed in all other groups. These results indicate that the CA has a remarkable effect in killing tumor cells by capturing hVEGF and suppressing angiogenesis at the tumor site compared to other aptamer complexes.

The invention claimed is:

1. An aptamer complex comprising a branched DNA, an aptamer corresponding to a target sequence, and a terminal DNA,
    wherein the branched DNA is a Y-shaped DNA,
    wherein the Y-shaped DNA is any one or more selected from the group consisting of SEQ ID NOs: 1 to 6 and
    wherein the aptamer corresponding to the target sequence is any one or more selected from the group consisting of SEQ ID NOs: 7 and 9.

2. The aptamer complex according to claim 1, wherein the protein corresponding to the target sequence is vascular endothelial growth factor (VEGF).

3. The aptamer complex according to claim 1, wherein the terminal DNA is any one or more selected from the group consisting of SEQ ID NOs: 13 and 14.

4. A drug delivery system comprising the aptamer complex of claim 1 as an active ingredient.

5. A pharmaceutical composition for treating a cancer, comprising the aptamer complex of claim 1 as an active ingredient.

6. The pharmaceutical composition for treating a cancer according to claim 5, wherein the cancer is any one or more selected from the group consisting of melanoma, small cell lung cancer, non-small cell lung cancer, brain tumor, liver cancer, thyroid tumor, gastric cancer, prostate cancer, breast cancer, ovarian cancer, bladder cancer, lung cancer, colorectal cancer, breast cancer, prostate cancer, glioblastoma, cervical cancer, endometrial cancer, kidney cancer, colon cancer, pancreatic cancer, esophageal carcinoma, head and neck tumor, mesothelioma, sarcoma, cholangioma, small intestine adenocarcinoma, childhood malignant cancer, and epidermal cancer.

7. A kit for diagnosing a cancer, comprising the aptamer complex of claim 1 as an active ingredient.

* * * * *

SEQUENCE LISTING

```
<160> NUMBER OF SEQ ID NOS: 14

<210> SEQ ID NO 1
<211> LENGTH: 45
<212> TYPE: DNA
<213> ORGANISM: Artificial Sequence
<220> FEATURE:
<223> OTHER INFORMATION: Y01-5

<400> SEQUENCE: 1
gctcctcgcc tgaagctcga tgaatagcgg tcagatccgt accta            45

<210> SEQ ID NO 2
<211> LENGTH: 45
<212> TYPE: DNA
<213> ORGANISM: Artificial Sequence
<220> FEATURE:
<223> OTHER INFORMATION: Y02-5

<400> SEQUENCE: 2
gctcctcgcc tgaagcttcg ttcgcaatac gaccgctatt catcg            45

<210> SEQ ID NO 3
<211> LENGTH: 45
<212> TYPE: DNA
<213> ORGANISM: Artificial Sequence
<220> FEATURE:
<223> OTHER INFORMATION: Y03-5

<400> SEQUENCE: 3
gctcctcgcc tgaagcttag gtacggatct gcgtattgcg aacga            45

<210> SEQ ID NO 4
<211> LENGTH: 41
<212> TYPE: DNA
<213> ORGANISM: Artificial Sequence
<220> FEATURE:
<223> OTHER INFORMATION: Y01-3

<400> SEQUENCE: 4
atccatgcct agactggcga taagtagctg tccgctcctc g                41

<210> SEQ ID NO 5
<211> LENGTH: 41
<212> TYPE: DNA
<213> ORGANISM: Artificial Sequence
<220> FEATURE:
<223> OTHER INFORMATION: Y02-3
```

<400> SEQUENCE: 5
gctacttatc gccagcataa cgcttgcttg tccgctcctc g        41

<210> SEQ ID NO 6
<211> LENGTH: 41
<212> TYPE: DNA
<213> ORGANISM: Artificial Sequence
<220> FEATURE:
<223> OTHER INFORMATION: Y03-3

<400> SEQUENCE: 6
agcaagcgtt atgcgtctag gcatggattg tccgctcctc g        41

<210> SEQ ID NO 7
<211> LENGTH: 64
<212> TYPE: DNA
<213> ORGANISM: Artificial Sequence
<220> FEATURE:
<223> OTHER INFORMATION: Y_Vapt

<400> SEQUENCE: 7
agcttcaggc gaggagccca ccccgtcttc agacaagag tgcaggggtg gcgaggagcg        60
gaca        64

<210> SEQ ID NO 8
<211> LENGTH: 26
<212> TYPE: DNA
<213> ORGANISM: Artificial Sequence
<220> FEATURE:
<223> OTHER INFORMATION: Pri_Vapt

<400> SEQUENCE: 8
cccgtcttcc agacaagagt gcaggg        26

<210> SEQ ID NO 9
<211> LENGTH: 75
<212> TYPE: DNA
<213> ORGANISM: Artificial Sequence
<220> FEATURE:
<223> OTHER INFORMATION: Phos_Vapt

<400> SEQUENCE: 9
tttttaagct tgtccgctcc tcgccacccc tgcactcttg tctggaagac ggggtgggct        60
cctcgcctga agctt        75

<210> SEQ ID NO 10
<211> LENGTH: 64
<212> TYPE: DNA
<213> ORGANISM: Artificial Sequence
<220> FEATURE:
<223> OTHER INFORMATION: Y_Sc

<400> SEQUENCE: 10
agcttcaggc gaggagccca ctattatgga accgaatttt gtttcatgtg gcgaggagcg        60
gaca        64

<210> SEQ ID NO 11
<211> LENGTH: 26
<212> TYPE: DNA
<213> ORGANISM: Artificial Sequence
<220> FEATURE:
<223> OTHER INFORMATION: Pri_Sc

<400> SEQUENCE: 11

```
tattatggaa ccgaattttg tttcat                                          26

<210> SEQ ID NO 12
<211> LENGTH: 75
<212> TYPE: DNA
<213> ORGANISM: Artificial Sequence
<220> FEATURE:
<223> OTHER INFORMATION: Phos_Sc

<400> SEQUENCE: 12
tttttaagct tgtccgctcc tcgccacatg aaacaaaatt cggttccata atagtgggct     60
cctcgcctga agctt                                                      75

<210> SEQ ID NO 13
<211> LENGTH: 13
<212> TYPE: DNA
<213> ORGANISM: Artificial Sequence
<220> FEATURE:
<223> OTHER INFORMATION: Blu_end

<400> SEQUENCE: 13
tgtccgctcc tcg                                                        13

<210> SEQ ID NO 14
<211> LENGTH: 13
<212> TYPE: DNA
<213> ORGANISM: Artificial Sequence
<220> FEATURE:
<223> OTHER INFORMATION: FAM_Blu_end

<400> SEQUENCE: 14
tgtccgctcc tcg                                                        13
```